(12) United States Patent
Davis et al.

(10) Patent No.: US 6,383,755 B1
(45) Date of Patent: May 7, 2002

(54) METHODS AND KITS FOR DETERMINING THE FIDELITY OF POLYMERASE CHAIN REACTION CONDITIONS

(75) Inventors: Gregory D. Davis, Mountain View; Helmut Wurst, Cupertino, both of CA (US)

(73) Assignee: Clontech Laboratories, Inc., Palo Alto, CA (US)

( * ) Notice: Subject to any disclaimer, the term of this patent is extended or adjusted under 35 U.S.C. 154(b) by 0 days.

(21) Appl. No.: 09/656,548

(22) Filed: Sep. 6, 2000

Related U.S. Application Data

(60) Provisional application No. 60/152,754, filed on Sep. 8, 1999.

(51) Int. Cl.$^7$ .......................... C12Q 1/68; C12P 19/34; C07H 21/02; C07H 21/04
(52) U.S. Cl. .................. 435/6; 435/91.1; 435/91.2; 536/23.1; 536/24.33
(58) Field of Search .................. 435/91.2, 6, 91.1; 536/24.33, 23.1

(56) References Cited

U.S. PATENT DOCUMENTS 5,427,929 A * 6/1995 Richards et al. ........... 435/91.2

OTHER PUBLICATIONS

Stratagene Catalog 1988.*
Wayne M. Barnes, "The fidelity of Taq polymerase catalyzing PCR is improved by an N–terminal deletion" *Gene*, 112 (1992) pp 29–35.
Cariello et al, "A novel bacteria reversion and forward mutation assay based on green fluorescent protein", *Mutation Research 414* (1998) 95–105.
Peter Halling, "Is random mutation more rational", *Nature Biotechnology*, vol. 14 Apr. 1996.
Lundberg et al., "High–fidelity amplification using a thermostable DNA polymerase isolated from *Pyrococcus furiosus*", *Gene* 108 (1991) 1–6.
Day et al. "Nucleotide analogs and new buffers improve a generalized method to enrich for low abundance mutations", *Nucleic Acids Research*, 1999, vol. 27. No. 8.
Cariello et al., Mutational analysis using denaturing gradient gel electrophoresis and PCR, *Mutation Research*, 288 (1993) 103–112.

Jin–Yao Mo et al, "Mutational Specificity od dnaE173 Mutator Associated with a Defect in the Catalytic Subunit of DNA Polymerase III of *Escherichia coli*", *J. Mol. Biol* (1991) 222, 925–936.
R. Craig Caldwell et al. "Randomization of Genes by PCR Mutagenesis" *PCR Methods Appl.* (1992) 2(1):28–33.
Brail et al. "Improved polymerase fidelity in PCR–SSCPA" *Mutation Research* 303(1993) 171–175.
Fromant et al. "Direct Random Mutagenesis of Gene–Sized DNA Fragments Using Polymerase Chain Reaction", *Analytical Biochemistry* 224, 347–353 (1995).
Leung et al. "A method for Random Mutagenesis of a Defined DNA segment using a modified polymerase chain reaction", *Technique—a Journal of Methods in Cell and Molecular Biology*, vol. 1, No. 1 (Aug.), 1989: pp. 11–15.
Sandy et al. "Genotypic analysis of mutations in Taq I restriction recognition sites by restriction fragment length polymorphism/polymerase chain reaction" *Proc.Natl., Acad. Sci USA* vol. 89, pp. 890–894, Feb. 1992 Biochemistry.
Tyagi et al. "Molecular Beacons Probes that Fluoresce upon Hybridization" *Nature Biotechnology*, vol. 14, Mar. 1996.
Vartanian et al. "Hypermutagenic PCR involving all four transitions and a sizeable proportion of transversions", *Nucleic Acids Research*, 1996, vol. 24, No. 14, 2627–2631.

* cited by examiner

*Primary Examiner*—Kenneth R. Horlick
*Assistant Examiner*—Alexander H. Spiegler
(74) *Attorney, Agent, or Firm*—Bret E. Field; Bozicevic, Field & Francis

(57) ABSTRACT

Methods are provided for evaluating the fidelity of a given set of polymerase chain reaction conditions. In the subject methods, a template polydeoxyribonucleotide is amplified under the to be evaluated polymerase chain reaction conditions, where the template polydeoxyribonucleotide includes a pseudo restriction endonuclease restriction site. The resultant amplified product population is then contacted with the corresponding restriction endonuclease and resultant cleavage products, if any, are detected. The fidelity of the polymerase chain reaction conditions is then derived from the detected cleavage products (or absence thereof). Also provided are kits for use in practicing the subject methods. The subject methods are suited for determining the fidelity of a given polymerase under PCR conditions, and are particularly suited for determining the fidelity of a thermostable polymerase under PCR conditions.

21 Claims, 4 Drawing Sheets

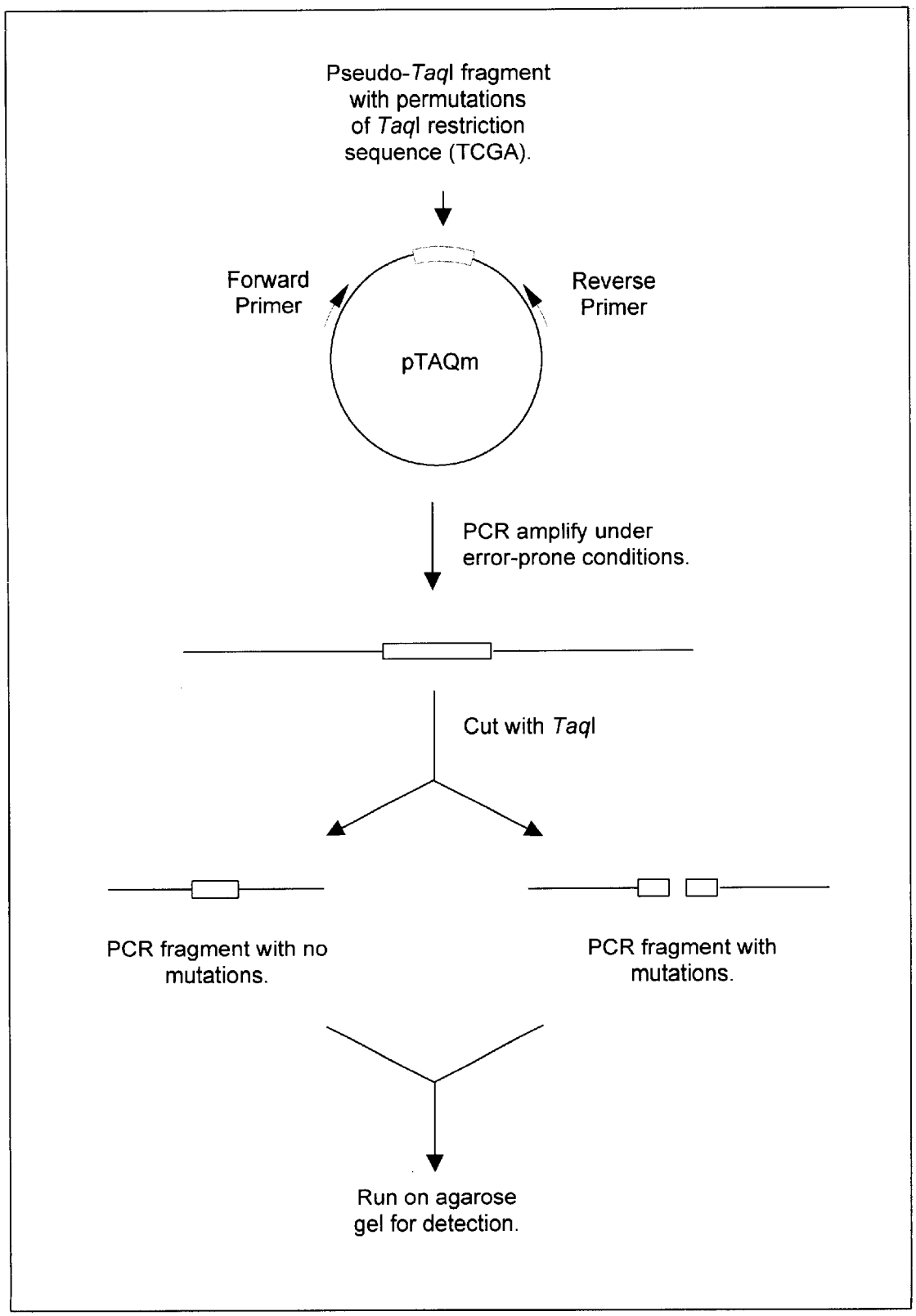
Figure 1. Detection of random mutations occuring during error-prone PCR by cutting with the *Taq*I restriction enzyme.

TCGA permutations which reflect the most common
PCR associated mutations.

A = tcga  (to detect A to G mutations)
B = tcga  (to detect T to C mutations)
C = tcga  (to detect G to A mutations)
D = tcga  (to detect C to T mutations)

Take these four permutations and incorporate them into an
oligonucleotide. Insert bases between TCGA permutations to reduce
hairpin formation.

```
       A       B      C      A       B      D      A       B
5'- tcga c tcga aa tcga g tcga tc tcga a tcga cg tcga g tcga tt - 3'
```

Add a complimentary oligonucleotide and 5' overhangs.

```
5'-GGGGTCGACTCGAAATCGGGTCGATCTCGAACGACGTCGAGTCGATT
   AGCTGAGCTTTAGCCCAGCTAGACTTGCTGCAGCTCAGCTAACCCC-5'
```

Pseudo-*TaqI* fragment

Create multimers by ligation, fill in the 5' overhangs, and blunt-end
clone the into pUC19 at *PvuII* site.

Figure 2. Design and cloning of the pseudo-*TaqI* fragment.

Figure 3. DNA sequence of insert region of pTAQm as determined by dye-terminination cycle sequencing. pUC19 DNA is shown in upper case and the pseudo-*TaqI* inserts are shown in lower case. The GGGG overhang sequences are higlighted at the boundry of each of the four inserts. No mutations were found to occur in the pseudo-*TaqI* sequence during cloning.

```
  1  CATTATTNTC ATNNCATTAC CCTATAAAAA TAGGNGTATC ACAGAGGCCC
 51  TTTCGTCTCG CGCGTTTCGG TGATGACGGT GAAAACCTCT GACACATGCA
101  GCTCCCGGAG ACGGGTCACA GCTTGTCTGT AAGCGNATGC CGGGAGCAGA
151  CAAGCCCGTC AGGGCGCGTC AGCGGGTGTT GGCGGGTGTC GGGGCTGGCT
201  TAACTATGCG GCATCAGAGC AGATTGTACT GAGAGTGCAC CATATGCGGT
251  GTGAAATACC GCACAGATGC GTAAGGAGAA AATACCGCAT CAGGCGCCAT
301  TCGCCATTCA GGCTGCGCAA CTGTTGGNAA GGGCGATCGG TGCGGGCCTC
351  TTCGCTATTA CGCCAGggg tcaacttgaa atcgggtcaa tcttgaaccg
401  acgtcaagtt gattgggtc aacttgaaat cgggtcaatc ttgaaccgac
451  gtcaagttga ttgggtcaa cttgaaatcg gtcaatctt gaaccgacgt
501  caagttgatt ggggtcaact tgaaatcggg tcaatcttga accgacgtca
551  agttgattgggCTGCATTA ATGAATCGGC CAACGCGCGG GGAGAGGCGG
601  TTTGCGTATT GGGCGCTCTT CCGCTT
```

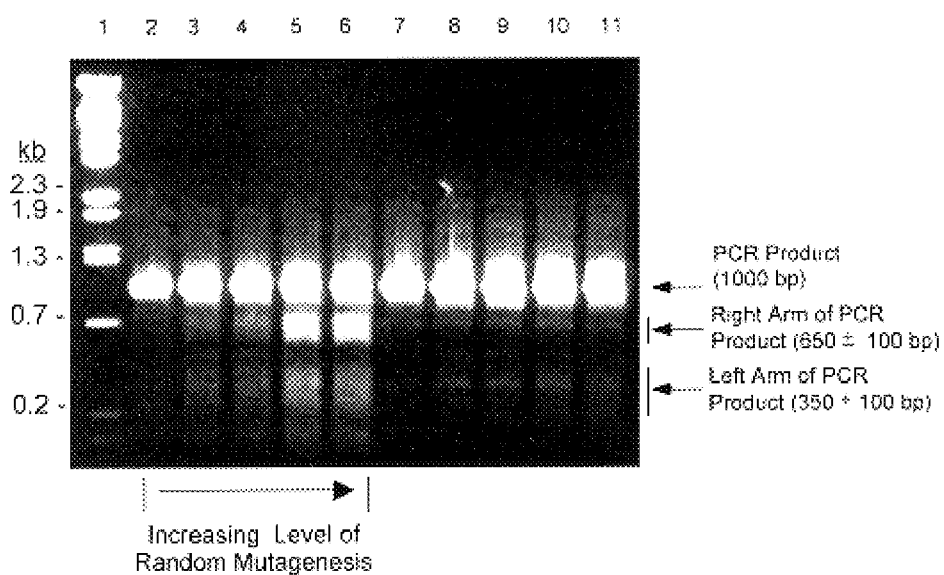
Figure 4. Detection of random mutations by *Taq*I restriction enzyme digestion. Lane 1, λ *Bst*EII marker; Lanes 2-6, error-prone PCR reactions 1, 2, 3, 4, and 5 which have been purified and digested with *Taq*I at 65°C for 1 hr (see Table 1 for reaction composition); Lanes 7-11, same as lanes 2-6 without *Taq*I enzyme.

SEQUENCE LISTING

```
<160> NUMBER OF SEQ ID NOS:  2

<210> SEQ ID NO 1
<211> LENGTH: 25
<212> TYPE: DNA
<213> ORGANISM: Artificial Sequence
<220> FEATURE:
<223> OTHER INFORMATION: primer

<400> SEQUENCE: 1
gagcctatgg aaaaacgcca gcaac                                              25

<210> SEQ ID NO 2
<211> LENGTH: 25
<212> TYPE: DNA
<213> ORGANISM: Artificial Sequence
<220> FEATURE:
<223> OTHER INFORMATION: primer

<400> SEQUENCE: 2
gcaaaaaagg gaataagggc gacac                                              25
```

METHODS AND KITS FOR DETERMINING THE FIDELITY OF POLYMERASE CHAIN REACTION CONDITIONS

CROSS REFERENCE TO RELATED APPLICATIONS

Pursuant to 35 U.S.C. §119(e), this application claims priority to the filing date of U.S. Provisional Patent Application Serial No. 60/152,754 filed Sep. 8, 1999, the disclosure of which is herein incorporated by reference.

INTRODUCTION

1. Technical Field

The field of this invention is the polymerase chain reaction.

2. Background of the Invention

The polymerase chain reaction (PCR), in which a polymerase (typically a thermostable polymerase) is used to produce amplified amounts of nucleic acids from an initial template nucleic acid, finds use in a number of diverse research, clinical, forensic and industrial applications.

One application where PCR finds use is in the study and modification of wild-type protein function by error-prone PCR mutagenesis (Leung et al., infra; Cadwell & Joyce, infra). In error-prone PCR, a gene of interest is amplified by PCR under buffer conditions which promote the random misincorporation of nucleotides. The pool of mutant genes from the error-prone PCR reaction is then cloned and used as a library to search for altered protein function.

In the past, the study of the types of mutations occurring in error-prone PCR has relied directly on DNA sequencing. The high cost and cumbersome work associated with sequencing large numbers of clones has limited the extent of experimentation with respect to error-prone PCR and mutational studies in general. As alternatives to sequencing, several phenotypic assays have been developed which detect mutations by observing losses in streptomycin resistance (Mo et al., infra), changes in the function of the lac operon (e.g. blue/white screening)(Lundberg et al., infra; Barnes, infra), and by reversion of a green fluorescent protein mutant (Cariello et al., infra). In addition, gel-based assays have been developed which include single-strand conformation polymorphism (SSCP) (Brail et al., supra) and denaturing gradient gel electrophoresis (DGGE) (Cariello and Skopek, infra).

While these assays can provide accurate information about the relative extents of mutation occurring in a homogenous gene population, they provide little information about the types of mutations occurring. In addition, the gel-based assays are inherently dependent on an electrophoretic separation for comparison of mutation rates, and the phenotypic methods all require ligation and cell transformation procedures associated with typical recombinant DNA cloning methods.

As such, there is a need for the development of alternative methods of evaluating the fidelity of a polymerase under a given set of PCR conditions. Of particular interest would be the development of a rapid in vitro assay which can easily quantify and characterize the relative levels of random mutations occurring in error-prone PCR.

Relevant Literature

References of interest include: Barnes, "The fidelity of Taq polymerase catalyzing PCR is improved by an N-terminal deletion," *Gene* (1992)112(1):29–35; Brail et al, "Improved polymerase fidelity in PCR-SSCPA," *Mutat. Res.* (1993) 303(4):171–5; Cadwell et al., "Randomization of genes by PCR mutagenesis," *PCR Methods Appl.* (1992) 2(1):28–33; Cariello & Skopek, "Mutational analysis using denaturing gradient gel electrophoresis and PCR," *Mutat.Res.* (1993) 288(1):103–112; Cariello et al., "A novel bacterial reversion and forward mutation assay based on green fluorescent protein," *Mutat. Res.* (1998) 414(1–3): 95–105; Day et al. "Nucleotide analogs and new buffers improve a generalized method to enrich for low abundance mutations," *Nuc. Acids Res.* (1999) 27(8): 1819–1827; Fromant et al., "Direct random mutagenesis of gene-sized DNA fragments using polymerase chain reaction," *Anal. Biochem.* (1995) 224(1):347–53; Halling, "Is random mutation more rational?" *Nat. Biotechnol.* (1996) 14(4):432, 436; Leung, "A method for random mutagenesis of a defined DNA segment using a modified polymerase chain reaction," *Technique* (1989) 1(1): 11–15; Lundberg et al., "High-fidelity amplification using a thermostable DNA polymerase isolated from Pyrococcus furiosus," *Gene* (1991) 108(1):1–6; Mo et al., "Mutational specificity of the dnaE173 mutator associated with a defect in the catalytic subunit of DNA polymerase III of *Escherichia coli,*"*J. Mol. Biol.* (1991) 222(4):925–36; Sandy et al., "Genotypic analysis of mutations in Taq I restriction recognition sites by restriction fragment length polymorphism/polymerase chain reaction," *Proc. Nat'l Acad. Sci. USA* (Feb. 1992) 89:890–894; Tyagi & Kramer, "Molecular beacons: probes that fluoresce upon hybridization," Nat. Biotechnol. (1996) 14(3):303–308; and Vartanian et al., "Hypermutagenic PCR involving all four transitions and a sizeable proportion of transversions," *Nucleic Acids Res.* (1996)24(14):2627–31.

SUMMARY OF THE INVENTION

Methods of determining the fidelity of a given set of polymerase chain reaction conditions are provided. In the subject methods, a template polydeoxyribonucleotide that includes a pseudo restriction endonuclease site is amplified under the polymerase chain reaction conditions to be evaluated. The pseudo restriction endonuclease site differs from its corresponding true restriction endonuclease site by at least one nucleotide substitution. The resultant amplified product population is then contacted with the corresponding restriction endonuclease and any resultant cleavage products are detected. The detected cleavage products, or absence thereof, are then related to the fidelity of the polymerase chain reaction conditions used to amplify the template polydeoxyribonucleotide. Also provided are kits for practicing the subject methods.

BRIEF DESCRIPTION OF THE FIGURES

FIG. 1 provides a schematic of one embodiment of the subject methods.

FIG. 2 provides a schematic for the synthesis of the template polydeoxyribonucleotide employed in the method depicted in FIG. 1.

FIG. 3 provides the nucleic acid sequence of the template polydeoxyribonucleotide of pTAQm which is employed in the method depicted in FIG. 1.

FIG. 4 shows the detection of TaqI cleavage products following error prone PCR of the template polydeoxyribonucleotide depicted in FIG. 2.

DEFINITIONS

The term "fidelity" refers the error frequency rate of a given polynucleotide amplification reaction, e.g. a given set of PCR conditions. An example of an error frequency rate is the number of mutations that occur for every 1000 bp of synthesized PCR product.

The term "nucleic acid" as used herein means a polymer composed of nucleotides, e.g. deoxyribonucleotides or ribonucleotides, and analogues thereof.

The terms "deoxyribonucleic acid" and "DNA" as used herein means a polymer composed of deoxyribonucleotides.

The term "oligonucleotide" as used herein denotes single stranded nucleotide multimers of from about 2 to 100 nucleotides in length.

The term "polynucleotide" as used herein refers to single or double stranded polymer composed of nucleotide monomers of greater than about 30 nucleotides in length, where the length of the polynucleotide may be as long as 1000 bp or longer, up to 8 to 10 kb or longer.

The term "polydeoxyribonucleotide" as used herein refers to single or double stranded polymer composed of deoxyribonucleotide monomers of greater than about 30 deoxyribonucleotides in length, where the length of the polydeoxyribonucleotide may be as long as 1000 bp or longer, up to 8 to 10 kb or longer.

The terms "pseudo restriction endonuclease site" and "pseudo restriction site" refer to a domain of nucleotides having a sequence that differs from the sequence recognized by a restriction endonuclease by at least 1 nucleotide. The number of differing nucleotides in the pseudo restriction as compared to the true restriction site is generally not more than 50 number % in many embodiments, e.g. if the site has a total of 4 nt, up to 2 nt may be different from the true site.

The terms "true restriction endonuclease site" and "true restriction site" refer to a domain of nucleotides having a sequence that is recognized and cleaved by a restriction endonuclease.

The terms "population of amplified product polydeoxyribonucleotides" and "amplified product population" refer to the collection of individual polydeoxyribonucleotides that are produced by amplification of a template DNA, e.g. by PCR.

The term "cleaved product population" refers to the collection of polydeoxyribonucleotides that results from contact of an amplified product population with a restriction enzyme.

DESCRIPTION OF THE SPECIFIC EMBODIMENTS

Methods for evaluating the fidelity of a polymerase chain reaction conditions are provided. In the subject methods, a template polydeoxyribonucleotide comprising a pseudo restriction endonuclease site is amplified under the polymerase chain reaction conditions to be evaluated. The resultant amplified product population is then contacted with the corresponding restriction endonuclease and any resultant cleavage products are detected. The presence or absence of resultant cleavage products is then used to derive the fidelity of the polymerase chain reaction conditions. Also provided are kits for practicing the subject methods. In further describing the subject invention, the methods will be reviewed first in greater detail, followed by a discussion of various applications in which the subject methods find use and a description of kits for practicing the subject methods.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Methods

As summarized above, the subject invention provides a method for evaluating the fidelity of a given set of PCR conditions. In other words, the subject invention provides a means of determining how error-prone a given set of PCR conditions is during the amplification of DNA. To evaluate the fidelity of a given set of PCR conditions, a template polydeoxyribonucleotide that includes a pseudo restriction endonuclease site is amplified under the to be evaluated polymerase chain reaction conditions. Following contact of the resultant population of amplified product polydeoxyribonucleotides with the corresponding restriction endonuclease, any resultant cleavage products are detected and the fidelity of the polymerase chain reaction conditions is derived therefrom.

A feature of the subject invention is that a template polydeoxyribonucleotide that includes a pseudo restriction endonuclease site is amplified using the polymerase chain reaction conditions whose fidelity is to be evaluated. By pseudo restriction endonuclease site is meant a site or domain of the template polydeoxyribonucleotide having a sequence of nucleotides which differs in sequence from its corresponding true endonuclease restriction site (i.e. the sequence of nucleotides recognized by a restriction endonuclease) by at least one nucleotide substitution. In other words, the pseudo restriction site found on the subject polydeoxyribonucleotides differs from its corresponding true restriction site by at least one nucleotide. In those embodiments where the pseudo restriction site differs from its corresponding true restriction site by more than one nucleotide residue, the number of differing residues usually does not exceed about 50 number % of the total number of residues in the restriction site, e.g. 2 residues for a 4 base long restriction site. In many embodiments, the pseudo restriction site will differ from its corresponding true restriction site by a single nucleotide.

Any given pseudo restriction site will be designed for use in detecting the presence of transition or transversion mutations. Where the pseudo restriction site is to provide detection of transition mutations, the single nucleotide substitution present in the pseudo restriction site will be: (a) a purine for a purine, i.e. an A will be replaced by a G or a G will be replaced by an A in the pseudo restriction site as compared to the corresponding true restriction site; or (b) a pyrimidine for a pyrimidine, i.e. a T will be replaced by a C or a C will be replaced by a T in the pseudo restriction site as compared to the corresponding true restriction site. Where the pseudo restriction site is to provide detection of transversion mutations, the single nucleotide substitution present in the pseudo restriction site will be a pyrimidine for a purine or vice versa, e.g. an A will be replaced by a T or a C, a G will be replaced by an C or a T, a T will be replaced by an A or a C will be replaced by an A or a G (i.e. A⇌T, A⇌C, T⇌G or C⇌G), in the pseudo restriction site as compared to the corresponding true restriction site.

In many embodiments, the pseudo restriction site will include at least one of the four different bases found in naturally occurring deoxyribonucleic acids, i.e. A, G, C and T. The length of a given pseudo restriction site, i.e. the number of individual bases in a given pseudo restriction site, will vary, but will generally be at least about 4 nt and may be as long as 34 nt or longer, but in many embodiments does not exceed about 8 nt and usually does not exceed about 6 nt.

The pseudo restriction site employed in the subject invention may correspond to a wide variety of different restriction sites, i.e. it may be a single nucleotide substitution mutant of any one of a number of different restriction sites, i.e. domains of DNA having a sequence recognized and cleaved by a restriction endonuclease. As such, the pseudo restriction site may correspond to a site recognized by any restriction endonuclease, where known restriction endonucleases include those listed in Table 1, infra. In many embodiments of the invention, the pseudo restriction site will be one that differs in sequence from one of the sequences shown in Table 1 by a single nucleotide. Other restriction enzymes of interest include BstZ17I, BsrG1, NsiI, etc.

TABLE 1

| Enzyme | Sequence | Enzyme | Sequence | Enzyme | Sequence | Enzyme | Sequence |
|---|---|---|---|---|---|---|---|
| CviJI | RGCY | CviQI | GTAC | AuaI | CYCGRG | SphI | GCATGC |
| MnlI | CCTC | RsaI | GTAC | Bsp1286I | GDGCHC | NaeI | GCCGGC |
| AluI | AGCT | TaqI | TCGA | AhaII | GRCGYC | NheI | GCTAGC |
| BsuFI | CCGG | TthHBI | TCGA | AosII | GRCGYC | BamFI | GGATCC |
| HapII | CCGG |  |  | BanII | GRCGYC | BamHI | GGATCC |
| HpaII | CCGG | ScrFI | CCNGG | HgiJII | GRCGYC | BamKI | GGATCC |
| MspI | CCGG | DdeI | CTNAG | AccI | GTMKAC | BamNI | GGATCC |
| AccII | CGCG | CuiBI | GANTC | HincII | GTYRAC | BstI | GGATCC |
| BstUI | CGCG | HhaII | GANTC | HgiAI | GWGCWC | Bst1503I | GGATCC |
| BsuEI | CGCG | HinfI | GANTC | Cfr10I | RCCGGY | NarI | CGCGCC |
| FnuDII | CGCG | Cfrl3I | GGNCC | MflI | RGATCY | ApaI | GGGCCC |
| ThaI | CGCG | Sau96I | GGNCC | XhoII | RGATCY | Asp718I | GGTACC |
| DpnI | G$^{m6}$ATC |  |  | HaeII | RGCGCY | KpnI | GGTACC |
| NanII | G$^{m6}$ATC | BcnI | CCSGG | NgoI | RGCGCY | SalI | GTCGAC |
| NmuDI | G$^{m6}$ATC | NciI | CCSGG | CfrI | YGGCCR | ApaLI | GTGCAC |
| NmuEI | G$^{m6}$ATC | AacI | CCWGG | EaeI | YGGCCR | HpaI | GTTAAC |
| Bce243I | GATC | AorI | CCWGG |  |  | AccIII | TCCGGA |
| BsaPI | GATC | ApyI | CCWGG | HindIII | AAGCTT | BspMII | TCCGGA |
| Bsp67I | GATC | AtuBI | CCWGG | MluI | ACGCGT | NruI | TCGCGA |
| BspAI | GATC | AtuII | CCWGG | SpeI | ACTAGT | Sbo13I | TCGCGA |
| BspPII | GATC | BinSI | CCWGG | BglII | AGATCT | XbaI | TCTAGA |
| BsrPII | GATC | BstGII | CCWGG | StuI | AGGCCT | AtuCI | TGATCA |
| BssGII | GATC | BstNi | CCWGG | BanIII | ATCGAT | BclI | TGATCA |
| BstEIII | GATC | Cfr5I | CCWGG | BspXI | ATCGAT | BstGI | TGATCA |
| BstXII | GATC | CfrllI | CCWGG | ClaI | ATCGAT | CpeI | TGATCA |
| CpaI | GATC | EcaII | CCWGG | Cfr6I | CAGCTG | BalI | TGGCCA |
| CviAI | GATC | EclII | CCWGG | PvuII | CAGCTG |  |  |
| DpnII | GATC | EcoRII | CCWGG | NdeI | CATATG | BstXI | CCAN$_6$TGG |
| FnuAII | GATC | Eco27I | CCWGG | NcoI | CCATGG | MstII | CCTNAGG |
| FnuCI | GATC | Eco38I | CCWGG | Cfr9I | CCCGGG | XmnI | GAAN$_4$TTC |
| FnuEI | GATC | MphI | CCWGG | SmaI | CCCGGG | BglI | GCCN$_5$GGC |
| MboI | GATC | MvaI | CCWGG | XmaI | CCCGGG | BstEII | GGTNACC |
| MmeII | GATC | TaqXI | CCWGG | SacII | CCGCGG |  |  |
| MnoIII | GATC | BbvI | GCAGC | PvuI | CGATCG | EcoK | AACN$_6$GTGC |
| MosI | GATC | AvaII | GGWCC | RshI | CGATCG | StySPI | AACN$_6$GTRC |
| MthI | GATC | Bme216I | GGWCC | XorII | CGATCG | EcoR124 | GAAN$_6$RTCG |
| NdeII | GATC | Eco47I | GGWCC | EagI | CGGCCG | EcoR124/3 | GAAN$_7$RTCG |
| NflI | GATC | SinI | GGWCC | XmaIII | CGGCCG | EcoA | GAGN$_7$GTCA |
| NlaII | GATC |  |  | BsuMI | CTCGAG | EcoDXXI | TCAN$_7$ATTC |
| NsiAI | GATC | EcoPI | AGACC | PaeR7I | CTCGAG | EcoB | TGAN$_8$TGCT |
| NsuI | GATC | MboII | GAAGA | XhoI | CTCGAG | StySBI | GAGN$_6$RTAYG |
| PfaI | GATC | HgaI | GACGC | PstI | CTGCAG |  |  |
| Sau3AI | GATC | SfaNI | GCATC | SflI | CTGCAG | CspI | CGGWCCG |
| SinMI | GATC | BinI | GGATC | EcoRI | GAATTC | RsrII | CGGWCCG |
| HhaI | GCGC | FokI | GGATG | RarI | GAATTC |  |  |
| HinPI | GCGC | HphI | GGTGA | Sso47I | GAATTC | NotI | GCGGCCGC |
| BsuRI | GGCC | BspMI | ACCTGC | SacI | GAGCTC | SfiI | GGCCN$_5$GGCC |
| HaeIII | GGCC |  |  | SstI | GAGCTC |  |  |
| NgoII | GGCC | AquI | CYCGRG | EcoRV | GATATC |  |  |

R = G or A; Y = C or T; M = A or C; K = G or T; S = G or C; W = A or T; H = A or C or T; B = G or T or C; V = G or C or A; D = G or A or T; N = A or C or G or T; m$^6$A = 6-methyladenine. (Reprinted, with permission, from McClelland and Nelson 1988.)

In one embodiment of the subject invention, the pseudo restriction site is a pseudo TaqI restriction site. By pseudo TaqI restriction site is meant a stretch of four nucleotides that varies in sequence from the sequence of the true TaqI restriction site, i.e. TCGA, by at least one nucleotide substitution, and in many embodiments a single nucleotide substitution. Specific pseudo TaqI restriction sites of interest include the following: TCAA (to detect A to G mutations); TCGG (to detect G to A mutations); TTGA (to detect T to C mutations); and CCGA (to detect C to T mutations); ACGA (to detect A to T mutations); TCGT (to detect T to A mutations); TAGA (to detect A to C mutations); TCTA (to detect T to G mutations); TGGA (to detect G to C mutations); TCCA (to detect C to G mutations); GCGA (to detect G to T mutations); and TCGC (to detect C to A mutations).

The template polydeoxyribonucleotide includes at least one pseudo restriction site, as described above. In many embodiments, the template polydeoxyribonucleotide includes a plurality of pseudo restriction sites, where by plurality is meant at least 2, usually at least 5 and more usually at least 10, where when a plurality of pseudo restriction sites are present, the number may be as great as 200 or greater, but generally does not exceed about 50 and usually does not exceed about 40. Where a plurality of pseudo restriction sites are present in the polydeoxyribonucleotide, the disparate pseudo restriction sites are generally substantially contiguous, by which is meant that they are sequentially positioned in the template polydeoxyribonucleotide, where a short intervening sequence may or may not be present between any two give pseudo restriction sites. When present, the intervening sequence ranges from 1 to 10, usually from 1 to 3 nucleotides in length and may be of any sequence, i.e. it is generally random.

In certain preferred embodiments, the pseudo restriction site(s) is generally located in a region of the template polydeoxyribonucleotide such that if the polydeoxyribonucleotide were cleaved at the pseudo restriction site, it would give rise to cleavage products of substantially equal length. By substantially equal length is meant that the length of the products varies by less than about 200 nt, usually less than about 100 nt and more usually less than about 50 nt. In these embodiments, the restriction site(s) is proximal to the center, or even at the center, of the template polydeoxyribonucleotide. By proximally located is meant that the pseudo restriction site(s) is within at least about 300 nt, usually at least about 150 nt and more usually at least about 50 nt of the center of the polydeoxyribonucleotide.

The template polydeoxyribonucleotide may vary in length, but is generally at least about 30 bp in length, usually at least about 50 bp in length and more usually at least about 100 bp in length, where in many embodiments the template polydeoxyribonucleotide is at least about 1,000 bp long and may be as long as 8,000 bp or 10,000 bp or longer, but generally will not exceed about 4,000 bp length and usually will not exceed about 3,000 bp in length. The template polydeoxyribonucleotide is generally a synthetic polymer, i.e. it is generally not a naturally occurring molecule. The template polydeoxyribonucleotide may be prepared using any convenient protocol. One convenient protocol is illustrated in the experimental section, infra, in which a polynucleotide is prepared through ligation of a plurality of oligonucleotides and inserted into a plasmid, where the template polydeoxyribonucleotide that includes the pseudo restriction site and is amplified in the subject methods, as described supra, includes sequence from both the inserted polynucleotide and the plasmid vector.

The template polydeoxyribonucleotide may be present in any convenient form. As such, the template polydeoxyribonucleotide may be a single or double stranded polynucleotide, such as a PCR product, fragment from a restriction digestion, present on a vector, etc. In many embodiments, the template polydeoxyribonucleotide is present on a vector, e.g. a plasmid. Where the vector is a plasmid, the plasmid will typically be from about 2.5 to 10 kbp, usually from about 3 to 8 kbp in length. The plasmid may be a previously known and even commercially available plasmid vector, or a custom made plasmid vector. A variety of plasmid vectors are known and include pBR322, pUC18, pUC19, pSP64, pSP65, pGEM-3Z, pGEM-3Zf-, pGEM-4, pGEM-4Z,πAN13, Bluescript M13+, Bluescript M13—, and the like.

In the subject methods, the first step is to amplify the above described template polydeoxyribonucleotide using the polymerase chain reaction conditions to be evaluated. The polymerase chain reaction (PCR), in which a nucleic acid primer extension product is enzymatically produced from template DNA (in this case the template polydeoxyribonucleotide) is well known in the art, being described in U.S. Pat. Nos.: 4,683,202; 4,683,195; 4,800,159; 4,965,188 and 5,512,462, the disclosures of which are herein incorporated by reference. The subject methods may be employed to evaluate the fidelity of any polymerase chain reaction conditions. By polymerase chain reaction conditions is meant the total set of conditions used in a given polymerase chain reaction, e.g. the nature of the polymerase or polymerases, the type of buffer, the presence of ionic species, the presence and relative amounts of dNTPs, etc.

To evaluate the fidelity of a given set of polymerase chain reaction conditions, the template polydeoxyribonucleotide, usually the plasmid vector into which the polydeoxyribonucleotide is incorporated, is first contacted with flanking primers, the polymerase or polymerases, and the other components of the PCR conditions whose fidelity is to be evaluated, where contact occurs under conditions sufficient to enzymatically produce primer extension product using the polydeoxyribonucleotide as template. Specifically, the template nucleic acid is contacted with flanking primers, the polymerase(s) and other reagents necessary and/or desirable for the PCR to proceed and which make up the to be evaluated polymerase chain reaction conditions. A critical feature of the subject invention is that the primers employed for this amplification step do not hybridize to a pseudo restriction site of the template polydeoxyribonucleotide, but instead hybridize to a region of the vector or template polydeoxyribonucleotide on either side of the one or more pseudo restriction sites present in the template polydeoxyribonucleotide.

The amount of template deoxyribonucleotide that is employed in the amplification reaction typically ranges from about 0.1 nM to 1.0 nM, usually from about 0.2 nM to 0.6 nM and more usually from about 0.3 nM to 0.5 nM. The flanking primers, typically oligonucleotide primers, employed in the PCR amplification procedure are of sufficient length to provide for hybridization to complementary template DNA at either end of the polydeoxyribonucleotide under annealing conditions (described in greater detail below) but will be of insufficient length to form stable hybrids with non-complementary template DNA. The primers will generally be at least 10 bp in length, usually at least 15 bp in length and more usually at least 16 bp in length and may be as long as 30 bp in length or longer, where the length of the primers will generally range from 18 to 50 bp in length, usually from about 20 to 35 bp in length. The template DNA (i.e. the polydeoxyribonucleotide) is generally contacted with a set of two primers, where the primers are typically complementary to the two 3' ends of the double stranded template DNA.

The polymerase reaction conditions may be characterized by the presence of one or more distinct polymerases. Of particular interest in many embodiments are thermostable polymerases. Known polymerases include: *Thermus aquaticus* DNA polymerase and mutants thereof, as described in U.S. Pat. Nos. 4,889,818; 5,352,600; 5,079,352; 5,405,774; 5,436,149; 5,446,591; 5,445,170; 5,556,772; 5,616,494; and 5,674,738, the disclosures of which are herein incorporated by reference, and other naturally occurring polymerase and mutants thereof, as described in U.S. Pat. Nos. 4,942,130; 4,946,786; 5,192,674; 5,210,036; 5,332,785; 5,374,553;

5,420,029; 5,489,523; 5,506,137; 5,545,552; 5,618,711 and 5,624,833, the disclosures of which are herein incorporated by reference. In certain embodiments, the PCR conditions are characterized by the presence of a single polymerase. In such embodiments, evaluation of the PCR conditions by the subject invention reveals information not only about the fidelity of the particular PCR conditions as a whole, but also about the fidelity of the polymerase under the specific PCR conditions. In other embodiments, the PCR conditions are characterized by the presence of two or more polymerases, e.g. a Family A polymerase and a Family B polymerase, Family B polymerases, etc. The PCR conditions are generally characterized by having from about 0.02U/µl to 0.6U/µl of the polymerase(s), usually from about 0.05 to 0.5 U/µl of the polymerase, where "U" corresponds to incorporation of 10 mmol dNTP into acid-insoluble material in 30 min at 74 EC.

Also present in the reaction mixture of the PCR conditions are deoxyribonucleoside triphosphates (dNTPs). Usually the reaction mixture comprises four different types of dNTPs corresponding to the four naturally occurring bases, i.e. dATP, dTTP, dCTP and dGTP. The reaction mixture further comprises an aqueous buffer medium which includes a source of monovalent ions, a source of divalent cations and a buffering agent. Any convenient source of monovalent ions, such as KCl, K-acetate, $NH_4$-acetate, K-glutamate, $NH_4Cl$, ammonium sulfate, and the like may be employed, where the amount of monovalent ion source present in the buffer will typically be present in an amount sufficient to provide for a conductivity in a range from about 500 to 20,000, usually from about 1000 to 10,000, and more usually from about 3,000 to 6,000 micro-ohms. The divalent cation may be magnesium, manganese, zinc and the like, where the cation will typically be magnesium. Any convenient source of magnesium cation may be employed, including $MgCl_2$, Mg-acetate, and the like. The amount of $Mg^{2+}$ present in the buffer may range from 0.5 to 10 mM, but will preferably range from about 1.0 to 5 mM. Representative buffering agents or salts that may be present in the buffer include Tris, Tricine, HEPES, MOPS and the like, where the amount of buffering agent will typically range from about 5 to 150 mM, usually from about 10 to 100 mM, and more usually from about 20 to 50 mM, where in certain preferred embodiments the buffering agent will be present in an amount sufficient to provide a pH ranging from about 6.0 to 9.5. Other agents which may be present in the buffer medium include chelating agents, such as EDTA, EGTA and the like and non-ionic detergents, such as Tween 20, Triton X 100, NP40, and the like.

In preparing the reaction mixture which makes up the polymerase chain reaction conditions, the various constituent components may be combined in any convenient order. For example, the buffer may be combined with primer, polymerase and then template DNA, or all of the various constituent components may be combined at the same time to produce the reaction mixture.

Following preparation of the reaction mixture, the reaction mixture is subjected to a plurality of reaction cycles, where each reaction cycle comprises: (1) a denaturation step, (2) an annealing step, and (3) a polymerization step. The number of reaction cycles will vary depending on the application being performed, but will usually be at least 15, more usually at least 20 and may be as high as 60 or higher, where the number of different cycles will typically range from about 20 to 40. For methods where more than about 25, usually more than about 30 cycles are performed, it may be convenient or desirable to introduce additional polymerase into the reaction mixture such that conditions suitable for enzymatic primer extension are maintained.

The denaturation step comprises heating the reaction mixture to an elevated temperature and maintaining the mixture at the elevated temperature for a period of time sufficient for any double stranded or hybridized nucleic acid present in the reaction mixture to dissociate. For denaturation, the temperature of the reaction mixture will usually be raised to, and maintained at, a temperature ranging from about 85 to 100, usually from about 90 to 98 and more usually from about 93 to 96° C. for a period of time ranging from about 1 to 120 sec, usually from about 5 to 60 sec.

Following denaturation, the reaction mixture will be subjected to conditions sufficient for primer annealing to template DNA present in the mixture. The temperature to which the reaction mixture is lowered to achieve these conditions will usually be chosen to provide optimal efficiency and specificity, and will generally range from about 50 to 75, usually from about 55 to 70° C. Annealing conditions will be maintained for a period of time ranging from about 15 sec to 60 sec.

Following annealing of primer to template DNA or during annealing of primer to template DNA, the reaction mixture will be subjected to conditions sufficient to provide for polymerization of nucleotides to the primer ends in manner such that the primer is extended in a 5' to 3' direction using the DNA to which it is hybridized as a template, i.e. conditions sufficient for enzymatic production of primer extension product. To achieve polymerization conditions, the temperature of the reaction mixture will typically be raised to or maintained at a temperature ranging from about 65 to 75, usually from about 67 to 73° C. and maintained for a period of time ranging from about 15 sec to 20 min, usually from about 30 sec to 5 min.

The above cycles of denaturation, annealing and polymerization may be performed using an automated device, typically known as a thermal cycler. Thermal cyclers that may be employed are described in U.S. Pat. Nos 5,612,473; 5,602,756; 5,538,871; and 5,475,610, the disclosures of which are herein incorporated by reference.

Of particular interest in many embodiments is amplification of the polydeoxyribonucleotide under error prone PCR conditions. A variety of error prone PCR conditions are known to those of skill in the art, and typically include one or more of, elevated levels of manganese ion and/or other metals, unequal amounts of dNTPs, nucleotide analogues, successive rounds of PCR cycling, polymerases lacking proofreading activity, polymerase mutants with altered base specificity, and the like. Error prone PCR conditions of interest include those described in: Cadwell et al., "Randomization of genes by PCR mutagenesis," *PCR Methods Appl.* (1992) 2(1):28–33; Fromant et al., "Direct random mutagenesis of gene-sized DNA fragments using polymerase chain reaction," *Anal. Biochem.* (1995) 224(1):347–53; Leung, "A method for random mutagenesis of a defined DNA segment using a modified polymerase chain reaction," *Technique* (1989) 1(1): 11–15; and Vartanian et al., "Hypermutagenic PCR involving all four transitions and a sizeable proportion of transversions," *Nucleic Acids Res.* (1996)24(14):2627–31.

Amplification of the template polydeoxyribonucleotide that includes the pseudo restriction site, as described above, results in the production of a population of amplified product polydeoxyribonucleotides. Depending on the particular amplification conditions employed in the amplification step, e.g. the particular polymerase employed, the relative amounts of dNTPs, etc., the resultant population of amplified product polynucleotides may or may not include product polydeoxyribonucleotides in which the pseudo restriction endonuclease site has mutated to its corresponding true restriction endonuclease site. Thus, where the amplification conditions are high fidelity conditions, the resultant product population of polydeoxyribonucleotides will have few, if any, members in which the pseudo restriction site in the template polydeoxyribonucleotide has been replaced with a true restriction site. Conversely, where the amplification conditions are low fidelity conditions, the resultant product population should contain a relatively large number of polydeoxyribonucleotides in which a true restriction endonuclease site replaces the pseudo site present in the template polydeoxyribonucleotide. The relative amounts of those member polydeoxyribonucleotides of the resultant product population that have a true restriction site as opposed to the pseudo site is a direct result of the fidelity of the amplification conditions employed to produce the amplified product population.

The amplified product population that results from the above described amplification step is then contacted with the restriction endonuclease(s) that corresponds to the pseudo restriction site present in the template polydeoxyribonucleotide. In other words, the restriction endonuclease(s) whose recognition or cleavage sequence is the corresponding true sequence of the pseudo sequence found in the original template polydeoxyribonucleotide is combined with the population of amplified product polydeoxyribonucleotides. For example, where a pseudo TaqI sequence is present in the original template polydeoxyribonucleotide, the amplified product population is combined with TaqI. Likewise, where a pseudo BamHI sequence is present in the original template polydeoxyribonucleotide, the amplified product population is combined with BamHI. While the nature of the pseudo restriction site dictates the restriction enzyme that is contacted with the product population in this step, a list of representative restriction enzymes that may be employed in this step is found in Table 1, supra. In certain embodiments, the pseudo restriction site is actually a nested site that may correspond to 2 or more different restriction enzymes, e.g. ATATACAT, which can be used to detect A to G mutations by using any restriction enzymes BstZ171 (recognizing GTATAC), BsrGI (recognizing TGTACA) and NsiI (recognizing ATGCAT). In such embodiments, it may be desirable to contact the amplification products with two or more of the corresponding restriction enzymes. Accordingly, this contacting step may be characterized as contacting the amplification products with at least one restriction enzyme.

The amplified product population is contacted or combined with the restriction enzyme that corresponds to the pseudo restriction site of the template polydeoxyribonucleotide under conditions sufficient for enzymatic cleavage of constituent members of the product population that have the true restriction site (i.e. those in which the pseudo site has mutated to the true site during the amplification process) to occur. Contact conditions are chosen such that substantially all of the constituent members of the product population having a true restriction site are cleaved, where by substantially all is meant at least 90 number %, usually at least 95 number % and more usually at least 99 number %.

Contact generally occurs by combining a given amount of restriction enzyme with a given amount of amplified product in an aqueous reaction mixture and incubating the aqueous reaction mixture at a sufficient temperature and for a sufficient period of time for cleavage to occur. The amount of restriction enzyme that is combined with the amplified product population typically depends on the amount of amplified product. For example, where one is working with 250 ng of amplified product, the amount of restriction enzyme employed generally ranges from about 0.05 to 150 U, usually from about 15 to 25 U. During incubation, the aqueous reaction mixture is maintained at a temperature ranging from about 15 to 80° C., usually from about 25 to 65° C. for a period of time ranging from about 5 to 120 min, usually from about 30 to 60 min.

Contact of the population of amplified product with the restriction enzyme, as described above, results in the cleavage of those members of the population that have the true restriction site. As such, this step results in the production of a cleaved product population characterized by the presence of cleavage products and/or full length polydeoxyribonucleotides. The amount of cleavage products produced in this step directly depends on the number of product polydeoxyribonucleotides of the amplified product population that have the true restriction site. Thus, where the amplified product population was produced under high fidelity amplification conditions, little or no cleavage products should be produced upon contact of the restriction enzyme with the amplified product population. Conversely, where the amplified product population was produced under low fidelity conditions, e.g. by error prone PCR, a relatively larger amount of cleavage product is produced by contacting the product population with restriction enzyme. As such, the relative amounts of cleavage products and full length polydeoxyribonucleotides present in the cleaved product population produced by contact of the amplified product population with the restriction enzyme is directly dependent on the fidelity of the conditions employed to produce the amplified product population.

The resultant cleaved product population is then assayed for the presence of cleavage products, if any. In other words, cleavage products, if any, are then detected in the resultant cleaved product population. The cleavage products may be detected using any convenient protocol. One means of detecting the resultant cleavage products is to size separate the constituent members of the cleaved product population and then detect the cleavage products. For example, the cleaved product population may be electrophoretically separated on a slab gel and the resultant gel bands visualized with a stain, e.g. ethidium bromide, as illustrated in the experimental section infra. Alternatively, one may contact the cleaved product population with labeled nucleotides, e.g. fluorescently labeled dNTPs, that can be specifically attached to the 5' overhangs of the cleavage products. In this embodiment, following separation of unbound labeled dNTPs from remainder of the mixture, the detection of fluorescently labeled product indicates the presence of cleavage products. In yet other embodiments, one may covalently label the 5' ends of the polynucleotides present in the cleaved product population and then separate the labeled product. The appearance of short and long bands indicates the presence of the cleavage products in the cleaved product population. The presence of cleavage products can be detected by a variety of methods, including: mass spectrometry, high performance liquid chromatography (HPLC), capillary electrophoresis, polyacrylamide electrophoresis, denaturing-gradient gel electrophoresis (DGGE), single-strand conformation polymorphism (SSCP), electron microscopy, atomic force microscopy, labeled DNA hybridization probes, molecular beacons (see Tyagi and Kramer, supra), ELISA methods, and labeling by chemical modification of the cleaved DNA products. The exact manner in which cleavage products are detected in the subject methods is not critical, with the only requirement being that one be able to distinguish the cleavage products from the remainder of the polynucleotides present in the cleaved product population.

Where desired, the cleavage products may be quantified. Any convenient quantification protocol may be employed, e.g. densitometry, spectroscopy (absorbance and/or fluorescence), colorimetry, autoradiography, scintillation, and the like.

The final step of the subject methods is the fidelity derivation step, in which the fidelity of the polymerase chain reaction conditions (i.e. the ability of the PCR conditions to replicate template DNA without errors) is derived from the presence or absence of detected cleavage products in the cleaved product population. In other words, the presence or absence of detected cleavage products is used to derive the fidelity of the PCR conditions that were employed to produce the population of amplified product polynucleotides. The nature of the fidelity information derived from the detected cleavage products may vary. Thus, where one is solely interested in whether a particular set of PCR conditions gives rise to mutations, the mere presence of cleavage products is sufficient to yield this information, i.e. that the polymerase chain conditions assayed are not high fidelity conditions. Alternatively, one may more specifically determine the fidelity of the polymerase chain conditions by looking at the amounts of cleavage product that are produced and deriving an error frequency rate, e.g. the mutation rate per 1000 bp, from the detected amounts of cleavage products. See the experimental section, infra.

Utility

The subject methods find use in a variety of different applications in which a determination of the fidelity of a polymerase under a given set of conditions, i.e. the fidelity of a given set of PCR conditions, is desired. One application in which the subject methods find use is in the determination of the fidelity of thermostable polymerases, particularly newly discovered or engineered thermostable polymerases. The subject methods also find use in serving as a standard for monitoring the level of random mutagenesis, e.g. in a mutagenesis process that employs error prone PCR to ultimately generate random proteins. The subject methods also find use in the identification of novel error prone PCR conditions, such as error prone PCR conditions that lack mutational bias, e.g. bias towards any one of the 12 types of substitution mutations. The subject methods find use in determining the fidelity of mutagenesis with respect to a wide range of polydeoxyribonucleotides of differing length, where the length may be 1, 2, 3, 4 kb or even longer.

Kits

Also provided are kits for practicing the subject methods. The kits according to the present invention include at least the template polydeoxyribonucleotide that includes the at least one pseudo restriction site. Typically, the template polydeoxyribonucleotide is present on a vector, e.g. a plasmid. In many embodiments, the kit also includes the restriction enzyme corresponding to the pseudo restriction site, e.g. TaqI where the pseudo restriction site is a TaqI pseudo restriction site, as described above. The subject kits may further comprise additional reagents which are required for or convenient and/or desirable to include for carrying out the amplification step of the subject methods, where such reagents include a polymerase or combination of polymerases, an aqueous buffer medium (either prepared or present in its constituent components, where one or more of the components may be premixed or all of the components may be separate), and the like, dNTPs, salts, e.g. manganese, detection agents, e.g. stains, labeled dNTPs, and the like. The various reagent components of the kits may be present in separated containers, or may all be pre-combined into a reagent mixture for combination with template DNA. Also present in the kit are instructions for carrying out the subject methods, where the instructions may be present on one or more of the packaging, a package insert, containers present in the kit, and the like.

The following examples are offered by way of illustration and not by way of limitation.

EXPERIMENTAL

A. Preparation of Polydeoxyribonucleotide that Includes a Pseudo TaqI Site

The design and sequence of the oligonucleotides used to create the pseudo-TaqI DNA fragment are shown in FIG. 2. The oligonucleotides were combined together in a ligation reaction using T4 DNA ligase (New England Biolabs) in order to polymerize the pseudo-TaqI fragment as much as possible. Following ligation, the 5' overhangs of the pseudo-TaqI DNA fragments were filled in using AdvanTaq DNA polymerase (Clontech) with dCTP and dGTP. The sample was then purified using a Chromaspin 200 column (Clontech). The entire sample was then loaded on a 2% agarose gel and a region of DNA from about 150 to 300 bp (3 to 6 pseudo-TaqI fragments) was removed and purified by gel extraction.

Using pUC19 as a parent vector, the vector pTAQm was constructed. pUC19 was cut with PvuII which removes a 322 bp fragment, including the entire multiple cloning site and two of the four TaqI sites present in pUC19. The gel purified pseudo-TaqI DNA fragment (approximately 150 bp to 300 bp) was then blunt end ligated into the PvuII linearized pUC19. Screening by colony PCR revealed a clone, pTAQm, which contained an insert. Sequencing revealed that the insert was composed of four pseudo-TaqI fragments resulting in a 196 bp insert (FIG. 3).

B. Preparation of Population of Amplified Product

Two oligonucleotides were designed which flanked the inserted pseudo-TaqI fragment. The forward primer, PTAQF (5'- GAGCCTATGGAAAAACGCCAGCAAC) (SEQ ID NO:01), is located 249 bp upstream from the pseudo-TaqI insert in pTAQm. The reverse primer, PTAQR (5'- GCAAAAAAGGGAATAAGGGCGACAC) (SEQ ID NO:02) is located 552 bp downstream from the pseudo-TaqI insert. Five PCR reactions known to have varying levels of fidelity (Cadwell & Joyce, supra) were set up with the compositions shown in Table 2.

TABLE 2

PCR reaction compositions for the TaqI In Vitro mutation assay.

| | | Volume (μl) Reaction # | | | | |
|---|---|---|---|---|---|---|
| | Conc. | 1 | 2 | 3 | 4 | 5 |
| PCR Grade dH$_2$O | | 40 | 38 | 36 | 34 | 32 |
| AdvanTaq Plus Buffer | 10X | 5 | 5 | 5 | 5 | 5 |
| MnSO$_4$ | 8.0 mM | 0 | 2 | 4 | 4 | 4 |
| *Error-prone dNTP mix | 50X | 1 | 1 | 1 | 1 | 1 |
| dGTP | 2 mM | 1 | 1 | 1 | 3 | 5 |
| PTAQF/R primer mix | 10 μM ea. | 1 | 1 | 1 | 1 | 1 |
| pTAQm template | 1 ng/μl | 1 | 1 | 1 | 1 | 1 |
| AdvanTaq Plus Enzyme | 1 rxn/μl | 1 | 1 | 1 | 1 | 1 |

*Error-prone dNTP mix is composed of 2 mM dATP, 10 mM dCTP, and 10 mM dTTP.

The cycling parameters were: 94° C. for 30 sec, 25×(94° C. for 15 sec, 55° C. for 30 sec, 68° C. for 1:30 min), 68°

C. 1:30 min, 4° C. for storage. The PCR reactions were then purified using Chromaspin 100 columns (Clontech).

C. Cleavage Reaction

For each purified PCR product, a 20 µl restriction digestion containing at least 250 ng of purified PCR fragment (approximately 15 µl), 2 µl of 10×TaqI restriction enzyme buffer, and 1 µl (20 U) of TaqI restriction enzyme was set up. dH$_2$O was added to bring the reactions to 20 µl. The reactions were incubated at 65° C. for 1 hr. Negative controls were made for each reaction by omitting the TaqI enzyme from the above restriction digestions and also incubating at 65 ° C. for 1 hr.

D. Detection

15 µl of each reaction was then combined with 3 µl of gel loading buffer and loaded onto a 1% agarose gel using ethidium bromide stain (0.1 µg /ml) in both the gel and the TAE running buffer. The results are shown in FIG. 4. The appearance of two shorter DNA fragments indicates that random mutations have resulted in the creation of TaqI sites in the region of the pseudo-TaqI insert (FIG. 4, lanes 2–6). The intensity of the shorter bands increases from samples 1 to 5 as expected due to higher levels of manganese and increases in the amount of dGTP in the reaction. The compositions of reactions 1, 3, and 5 have been determined to result in a mutation rate of 2.0, 4.6, and 8.1 mutations per 1000 bp, respectively, as confirmed by DNA sequencing (data not shown). A comparison of these values to the band intensities in lanes 2, 4, and 6 (FIG. 4) is in agreement with an increased level of mutagenesis. Lanes 7 through 11 illustrate that the smaller fragments are a result of the TaqI digestion and not background generated under the differing conditions of error-prone PCR in reactions 1 through 5.

It is evident from the above results and discussion that a novel means for evaluating a given set of polynucleotide amplification reaction conditions is provided. As the subject methods are in vitro, disadvantages associated with in vivo methods are avoided. Furthermore, the subject methods provide rapid results and can be used to easily quantify and characterize the level of random mutations occurring under a given set of amplification reaction conditions, such as error prone PCR conditions. Furthermore, the subject invention provides a means for determining the types of mutations that occur under a given set of PCR conditions, e.g. whether transversion or transition mutations occur. Accordingly, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of evaluating the fidelity of a given set of polymerase chain reaction conditions, said method comprising:
    (a) amplifying a template polydeoxyribonucleotide under said polymerase chain reaction conditions using flanking primers to produce a population of amplified product polydeoxyribonucleotides, wherein said template polydeoxyribonucleotide comprises at least one pseudo restriction endonuclease site;
    (b) contacting said population of amplified product polydeoxyribonucleotides with at least one restriction endonuclease corresponding to said at least one pseudo restriction endonuclease site to produce a cleaved product population;
    (c) detecting the presence of cleavage products in said cleaved product population; and (d) relating the presence of said cleavage products to the fidelity of said polymerase chain reaction conditions;

whereby the fidelity of said polymerase chain reaction conditions is evaluated.

2. The method according to claim 1, wherein said pseudo restriction endonuclease site has a sequence that varies from a true restriction endonuclease site by at least one base substitution.

3. The method according to claim 1, wherein said template polydeoxyribonucleotide is present on a vector.

4. The method according to claim 1, wherein said pseudo endonuclease restriction site is positioned near the center of said template polydeoxyribonucleotide.

5. The method according to claim 1, wherein said detecting comprises electrophoretically separating said cleaved product population.

6. A method of evaluating the fidelity of a polymerase, said method comprising:

(a) contacting a template polydeoxyribonucleotide present on a vector with flanking primers and said polymerase under polymerase chain reaction conditions to produce a population of amplified product polydeoxyribonucleotides, wherein said template polydeoxyribonucleotide comprises at least one pseudo restriction endonuclease site that varies from a true restriction endonuclease site by a single base substitution;

(b) contacting said population of amplified product polydeoxyribonucleotides with at least one restriction endonuclease corresponding to said at least one pseudo restriction endonuclease site to produce a cleaved product population;

(c) electrophoretically separating said cleaved product population and detecting the presence of cleavage products in said cleaved product population; and (d) relating the presence of said cleavage products to the fidelity of said polymerase;

whereby the fidelity of said polymerase is evaluated.

7. The method according to claim 6, wherein said pseudo endonuclease restriction site is positioned near the center of said template polydeoxyribonucleotide.

8. The method according to claim 6, wherein said vector is a plasmid.

9. The method according to claim 6, wherein said polymerase is a thermostable polymerase.

10. The method according to claim 6, wherein said endonuclease cleaves a restriction site that ranges in length from about 4 to 34 bp.

11. The method according to claim 6, wherein said template polydeoxyribonucleotide ranges in length from about 30 bp to 10 kbp.

12. A method of evaluating the fidelity of a thermostable polymerase, said method comprising:

(a) contacting a template polydeoxyribonucleotide present on a plasmid with flanking primers and said thermostable polymerase under polymerase chain reaction conditions to produce a population of amplified product polydeoxyribonucleotides, wherein said template polydeoxyribonucleotide comprises at least one pseudo TaqI restriction endonuclease cleavage site which varies from the true TaqI restriction endonuclease cleavage site by a single base substitution;

(b) contacting said population of amplified product polydeoxyribonucleotides with TaqI to produce a cleaved product population;

(c) electrophoretically separating said cleaved product population and detecting the presence of TaqI cleavage products in said cleaved product population; and (d) relating the presence of said TaqI cleavage products to the fidelity of said thermostable polymerase;

whereby the fidelity of said thermostable polymerase is evaluated.

13. The method according to claim 12, wherein said pseudo TaqI restriction site is positioned near the center of said template polydeoxyribonucleotide.

14. The method according to claim 12, wherein said template polydeoxyribonucleotide ranges in length from about 30 bp to 10 kbp.

15. A kit for use in determining the fidelity of a given set or polymerase chain reaction conditions, said kit comprising;

a template polydeoxyribonucleotide comprising at least 5 sequentially positioned pseudo restriction endonuclease sites of the same restriction endonuclease, wherein said pseudo restriction endonuclease sites are spaced apart from each other by an intervening sequence ranging from 1 to 10 nt in length; and instructions for practicing the method according to claim 1.

16. The kit according to claim 15, wherein said kit further comprises a restriction endonuclease corresponding to said pseudo restriction endonuclease site present in said template polydeoxyribonucleotide.

17. The kit according to claim 15, wherein said template polydeoxyribonucleotide is present on a vector.

18. The kit according to claim 15, wherein said kit further comprises primers.

19. The kit according to claim 15, wherein said kit further comprises dNTPs.

20. The kit according to claim 15, wherein said restriction endonuclease is TaqI.

21. The kit according to claim 15, wherein said intervening sequence ranges from 1 to 3 nt in length.

* * * * *